United States Patent
Zech et al.

(10) Patent No.: US 10,952,933 B2
(45) Date of Patent: Mar. 23, 2021

(54) KIT OF PARTS CONTAINING A CATIONICALLY HARDENABLE COMPOSITION AND USE AS DENTAL RETRACTION MATERIAL

(71) Applicant: 3M INNOVATIVE PROPERTIES COMPANY, St. Paul, MN (US)

(72) Inventors: Joachim Zech, Kaufering (DE); Hendrik Grupp, Ammersee (DE); Christoph Schulte, Windach (DE); Andreas R. Maurer, Langenneufnach (DE); Peter U. Osswald, Tuerkheim (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 97 days.

(21) Appl. No.: 15/741,812

(22) PCT Filed: Jun. 30, 2016

(86) PCT No.: PCT/US2016/040365
§ 371 (c)(1),
(2) Date: Jan. 4, 2018

(87) PCT Pub. No.: WO2017/007676
PCT Pub. Date: Jan. 12, 2017

(65) Prior Publication Data
US 2018/0200156 A1 Jul. 19, 2018

(30) Foreign Application Priority Data
Jul. 7, 2015 (EP) .................................... 15175679

(51) Int. Cl.
*A61K 6/10* (2006.01)
*A61K 6/90* (2020.01)
*A61K 6/18* (2020.01)
*A61K 6/61* (2020.01)
*A61K 6/70* (2020.01)
*A61K 6/891* (2020.01)

(52) U.S. Cl.
CPC .................. *A61K 6/90* (2020.01); *A61K 6/18* (2020.01); *A61K 6/61* (2020.01); *A61K 6/70* (2020.01); *A61K 6/891* (2020.01)

(58) Field of Classification Search
CPC ........... A61K 6/0011; A61K 6/18; A61K 6/90
See application file for complete search history.

(56) References Cited

U.S. PATENT DOCUMENTS

| 3,453,242 A | 7/1969 | Schmitt |
| 3,729,313 A | 4/1973 | Smith |
| 3,741,769 A | 6/1973 | Smith |
| 3,808,006 A | 4/1974 | Smith |
| 4,167,618 A * | 9/1979 | Schmitt ............. C08G 73/0213 528/424 |
| 4,250,053 A | 2/1981 | Smith |
| 4,394,403 A | 7/1983 | Smith |
| 4,657,959 A | 4/1987 | Bryan |
| 5,249,862 A | 10/1993 | Herold |
| 5,286,105 A | 2/1994 | Herold |
| 5,464,131 A | 11/1995 | Keller |
| 5,569,691 A | 10/1996 | Guggenberger |
| 5,743,981 A | 4/1998 | Lu |
| 5,750,589 A | 5/1998 | Zech |
| 5,918,772 A | 7/1999 | Keller |
| 6,043,295 A | 3/2000 | Oxman |
| 6,084,004 A | 7/2000 | Weinmann |
| 6,395,801 B1 | 5/2002 | Bissinger |
| 8,526,084 B2 | 9/2013 | Weyermann |
| 2001/0004082 A1 | 6/2001 | Keller |
| 2003/0153726 A1 * | 8/2003 | Eckhardt .................. A61K 6/10 528/423 |
| 2004/0146713 A1 | 7/2004 | Schaub |
| 2005/0200585 A1 | 9/2005 | Igarashi |
| 2006/0069180 A1 | 3/2006 | Bublewitz |
| 2006/0106127 A1 | 5/2006 | Klettke |

(Continued)

FOREIGN PATENT DOCUMENTS

| AU | 6857087 | 8/1987 |
| DE | 3737552 | 5/1989 |

(Continued)

OTHER PUBLICATIONS

Wypych, G. Handbook of Fillers, 4th ed.; ChemTec Publishing: Toronto, 2016; pp. 109-112. (Year: 2016).*

(Continued)

*Primary Examiner* — Michael F Pepitone
(74) *Attorney, Agent, or Firm* — 3M IPC

(57) ABSTRACT

The invention relates to a kit of parts comprising a Base Paste (B) and a Catalyst Paste (C), Base Paste (B) comprising a cationically hardenable component, Catalyst Paste (C) comprising a starter component suitable to contribute to the hardening of the cationically hardenable compound, the composition obtained when combining the compositions of Base Paste (B) and Catalyst Paste (C) comprising in addition a porous water-adsorbing component and water, the porous water-adsorbing component being selected from molecular sieves, zeolites, silica gel and mixtures thereof, wherein either the porous water-adsorbing component is present in Base Paste (B) and the water is present in Catalyst Paste (C), or the water-adsorbing component is present in Catalyst Paste (C) and the water is present in Base Paste (B). The invention also relates to a dental retraction composition obtainable by mixing Base Paste (B) and Catalyst Paste (C) and to a process of taking a dental impression and/or conducting a dental retraction using the kit of parts.

20 Claims, 1 Drawing Sheet

(56) References Cited

U.S. PATENT DOCUMENTS

| | | |
|---|---|---|
| 2007/0090079 A1 | 4/2007 | Kelller |
| 2008/0220050 A1 | 9/2008 | Chen |
| 2010/0035213 A1 | 2/2010 | Lubbers |
| 2010/0255443 A1 | 10/2010 | Dragan |
| 2011/0046262 A1 | 2/2011 | Bublewitz |
| 2012/0187017 A1* | 7/2012 | Zech ................ A61K 6/10 206/524.1 |
| 2014/0138864 A1 | 5/2014 | Plaumann |
| 2014/0170596 A1 | 6/2014 | Angeletakis |

FOREIGN PATENT DOCUMENTS

| | | |
|---|---|---|
| EP | 0231420 | 8/1987 |
| EP | 1776080 | 4/2007 |
| EP | 2442778 | 4/2012 |
| WO | WO 2005-016783 | 2/2005 |
| WO | WO 2007-016295 | 2/2007 |
| WO | WO 2007-047381 | 4/2007 |
| WO | WO 2007-104037 | 9/2007 |
| WO | WO 2009-061884 | 5/2009 |
| WO | WO 2009-092568 | 7/2009 |
| WO | WO 2009-151983 | 12/2009 |
| WO | WO 2015-086646 | 6/2015 |
| WO | WO 2016-196048 | 12/2016 |

OTHER PUBLICATIONS

"Ullmanns Enzyklopadie der industriellen Chemie", 4th edition, vol. 11, pp. 469.

Houben-Weyl, "Methoden der Organischen Chemie", 1985, vol. E5/Part 1, pp. 659 ff.

International Search Report for PCT International Application No. PCT/US2016/040365, dated Aug. 19, 2016, 5pgs.

* cited by examiner

KIT OF PARTS CONTAINING A CATIONICALLY HARDENABLE COMPOSITION AND USE AS DENTAL RETRACTION MATERIAL

CROSS REFERENCE TO RELATED APPLICATIONS

This application is a national stage filing under 35 U.S.C. 371 of PCT/US2016/040365, filed Jun. 30, 2016, which claims the benefit of EP Application No. 15175679.8, filed Jul. 7, 2015, the disclosures of each of which are incorporated by reference herein in their entirety.

FIELD OF THE INVENTION

The invention relates to a kit of parts containing a base paste and a catalyst paste and a cationically curing dental composition obtainable by combining those pastes. The dental composition is in particular useful as dental retraction material and if desired also for taking dental impressions. The cationically curable dental composition has the ability to keep a gingival sulcus open.

BACKGROUND ART

Producing dental replacement parts like crowns and bridges requires the exact determination of the dental situation in the mouth of the patient. Otherwise, the dental replacement parts will not accurately fit.

For determining the dental situation in the mouth of a patient different methods are known. Besides imaging and computer based methods, a huge portion of this task is still accomplished by using conventional dental impression materials.

Dental impression materials can be classified according to their curing mechanism (e.g. addition curing or condensation curing). Dental impression materials can also be classified according to their consistency. Besides low viscous dental impression materials, there exists highly viscous, so-called putty like dental impression materials.

Dental impression materials are typically provided as two component systems which consist of a base and a catalyst paste and which are mixed before use.

The materials are typically pasty and cure in the mouth of the patient due to a chemical curing mechanism. The cured material is removed from the mouth of the patient and the obtained impression represents a negative image of the dental situation. The impression is then typically filled with plaster to obtain a positive model. The positive model is used for designing the desired dental replacement part.

Producing an exact fitting dental replacement part requires not only the determination of the supragingival situation of the dental situation in the mouth of the patient, but also to some extend the subgingival situation, that is the situation beyond the visible gumline.

To make this region "accessible", currently often a dental retraction cord is used, which is inserted, e.g. with the help of a pincer, into the sulcus of a dental preparation. The dental retraction cord typically contains astringent agents and is sufficiently stiff to exert pressure on the surrounding tissue. The dental retraction cord is left in the sulcus for a sufficient period of time to effect a retraction, i.e. to keep the sulcus open for receiving a dental impression material to also record the surface structure which was beyond the gumline before. This procedure is pretty time consuming. Meanwhile dental retraction pastes having a high viscosity are available for addressing this issue.

However, both dental retraction cords and dental retraction pastes require additional steps in the impression procedure because they first have to be applied into the sulcus then they have to be removed either mechanically in the case of dental retraction cords or by rinsing off in the case of dental retraction pastes.

US 2003/0153726 A1 (Eckhardt et al.) describes a catalyst component containing at least one Broensted acid, water, at least one antacid-acting compound, optionally inert diluent and optionally modifier(s). The catalyst paste is intended for curing two-component N-alkylaziridino-group-containing preparations.

US 2014/0170596 A1 (Angeletakis) describes a retraction impression material based on VPS technology which expands and comprises hemostatic agents.

US 2010/255443 A1 (Dragan) describes a dental retraction material with enhanced fluid absorption. The material mainly consist of water, aluminium chloride, fumed silica and a fluid absorbing agent (e.g. silica gel, starch, polyacrylate).

WO 2009/092568 A2 (Bublewitz et al.) relates to a pasty mass used as insert material for widening the gingival sulcus comprising a paste-forming agent, superabsorber particles and an astringent.

US 2008/0220050 (Chen et al.) describes a composition for gingival retraction comprising clay, a glass filler, an astringent agent and water.

US 2010/0035213 A1 (Lubbers et al.) describes a method for retracting the sulcus of a tooth, using an expanding silicone material which expands upon curing.

EP 1 776 080 B1 (Dentsply) claims a method or taking a dental impression of a dentition including sub-gingival parts comprising the steps of (i) conditioning the dentition including sub-gingival parts with a certain wetting agent; (ii) contacting the dentition with a certain dental impression material, whereby the dental impression material is allowed to flow into sub-gingival parts, further comprising the step of preparing the dentition with a certain gingival retraction cord.

Thus, there is still room for improvement especially with regard to the requirements to be fulfilled with respect to modern dental materials.

DESCRIPTION OF THE INVENTION

In particular, there is a demand for a means or composition enabling the practitioner to combine the dental retraction step with the dental impression procedure in such a way that the dental impression material can be inserted directly into the sulcus where it leads to a retraction of the sulcus.

The composition should be easy to prepare and apply and have a moldable consistency.

Ideally, there is no need for a removal of the dental retraction material from the sulcus before the dental impression step is done. If possible, the means or composition should also have a sufficient shelf-life.

In one embodiment the present invention features a kit of parts comprising a Base Paste (B) and a Catalyst Paste (C),
Base Paste (B) comprising a cationically hardenable compound,
Catalyst Paste (C) comprising a starter component suitable to contribute to, start or initiate the hardening of the cationically hardenable compound, the composition obtained when combining the compositions of Base Paste (B) and Catalyst Paste (C) comprising in addition a porous water-adsorbing component and water, the porous water-adsorbing component being selected from molecular sieves, zeolites, silica gel and mixtures thereof, wherein the water-adsorbing component is present either in Base Paste (B) and the water is present in Catalyst Paste (C), or the water-adsorbing component is present in Catalyst Paste (C) and the water is present in Base Paste (B).

Thus, the porous water-adsorbing component and water are separated from each other before use, i.e. before the Base Paste (B) and the Catalyst Paste (C) are mixed.

In another embodiment, the invention relates to a composition for use as dental retraction material or dental impression material, the composition being obtainable by mixing the compositions of Base Paste (B) and Catalyst Paste (C) of the kit of parts described in the present text, the composition being characterized by at least one of the following features:
consistency: equal or less than 26 mm determined according to ISO 4823;
Shore hardness A: 40-90 determined according to DIN 53505 24 h after mixing the compositions of Base Paste (B) and Catalyst Paste (C);
showing a residual gap of more than 2.0 mm, preferably at least 3.0 mm, most preferred at least 4.0 mm, if determined according to the measurement described in the examples section.

According to a further embodiment, the invention is directed to a process for taking a dental impression including the subgingival parts and/or conducting a dental retraction, the process comprising the steps of
providing a kit of parts comprising the Base Paste (B) and Catalyst Paste (C) as described in the present text
combining the Base Paste (B) and Catalyst Paste (C) to obtain a dental composition,
applying the dental composition to dental tissue,
letting the dental composition harden,
removing the dental composition from the dental surface.

The invention is also related to the use of a microporous water-adsorbing component as described in the present text in combination with water for increasing the consistency of a hardenable composition (comprising a cationically hardenable compound) as described in the present text and a starter component (suitable to contribute to, initiate or start the hardening of the cationically hardenable compound) as described in the present text.

Moreover, the invention features a dental retraction composition obtained or obtainable by mixing a Base Paste (B) and a Catalyst Paste (C), Base Paste (B) comprising a cationically hardenable compound, the cationically hardenable compound being as described in the present text, Catalyst Paste (C) comprising a starter component, the starter component being suitable to contribute to the hardening of the cationically hardenable compound, the starter component being as described in the present text.

Unless defined differently, for this description the following terms shall have the given meaning:

The term "compound" or "component" is a chemical substance which has a particular molecular identity or is made of a mixture of such substances, e.g., polymeric substances.

By "paste" is meant a soft, viscous mass of solids dispersed in at least one liquid or a soft, viscous mass of a polymer.

A "particle" or "particulate filler" means a substance being a solid having a shape which can be geometrically determined. The shape can be regular or irregular. Particles can typically be analyzed with respect to e.g. grain size and grain size distribution. A particulate filler is composed of free-flowing particles. "Free-flowing" means that the particulate filler can be sieved, that is, it behaves like dry powdered sugar.

Polymeric particle(s) include organic polymeric material(s) and/or silicone elastomeric material(s), especially silicone elastomers comprising dimethylsiloxane units.

A porous component is defined as "water-adsorbing" if the component is able to reversibly adsorb water on its surface, in particular by inclusion of water in its pores without undergoing a chemical reaction with water.

"Elastomeric" means rubber-elastic or rubber-like. Elastomeric materials can be characterized e.g. by a certain tensile strength and/or elongation at break. Other means for characterizing elastomeric materials include the measurement e.g. of the Young's modulus. Elastomeric materials typically have an E-modulus in the range from 0.8 to 10 MPa or from 1 to 8 MPa or from 1.5 to 6 MPa (determined e.g. according to DIN 53504, thickness of sample: 2 mm).

A "hardenable compound" is any compound which can be cured or solidified e.g. by chemical crosslinking. Chemical crosslinking can be initiated by using a redox or ionic initiator, radiation or heating thereby typically leading to a significant change in rheological properties like viscosity.

A "starter or initiator" is a substance or a group of substances being able to start or initiate or contribute to the hardening process of a hardenable compound.

"Radiation sensitive" means that the composition or a part of the composition is sensitive towards radiation and generates or helps to generate reactive species when exposed to the radiation. Those reactive species typically include radicals (charged or not charged), ions and mixtures thereof.

"Radiation curable" means that the composition can be cured or hardened using radiation alone or in combination with other initiators or starters, including redox initiators. The radiation typically comprises wavelength in the range from 250 to 1000 nm or from 350 nm to 700 nm.

The terms "vulcanizing", "hardening", "polymerizing", "crosslinking", "curing" and "setting" are used interchangeable and refer to compositions that have as a common attribute the development of a crosslinked polymer from relatively low molecular weight linear or branched polymers or pre-polymers by means of a chemical reaction that simultaneously forms these crosslinks and effectively extends chain length at room temperature.

"Poly" means that the respective substance contains at least 10 repeating units of a certain monomer moiety.

The term "crosslinked polymer" refers to polymers that are the result of the reaction of the functional group or groups of the polymer chains or prepolymers that were lengthened or connected, e.g., to form a crosslinked network. In contrast to a thermoplastic polymer (i.e., a polymer that softens and flows upon heating) a crosslinked polymer, after crosslinking, is characteristically incapable of further flow.

The term "cationically polymerizable compound" is defined as a compound which can be polymerised using an initiator containing or being able to generate cations, especially reactive cations.

A "prepolymer" is defined as a compound or mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture or a crosslinked polymer with increased molecular weight compared to the prepolymer.

"Aziridines" are a group of organic compounds sharing the aziridine functional group, which is a three membered heterocycle with one amine group and two methylene groups. The parent compound of the aziridines is called aziridine with molecular formula $C_2H_5N$.

An "alkyl-substituted aziridino group" is an aziridine group, wherein at least one of the hydrogen atoms of the methylene groups is substituted by an alkyl group, preferably by a C1 to C4 alkyl group, e.g. methyl, ethyl, n- and iso-propyl or n-, iso- or tert.-butyl group. In the chemical literature a "methyl substituted aziridine" is sometimes also referred to as "propylene imine".

"Polyether" or "polyether group containing compound" are compounds having a molecular weight of at least 150 g/mol and containing in the backbone at least 3, 10 or 20 ether moieties. Polyether containing compositions used as dental impression material can be cured by different mechanisms. Widely used is a crosslinking reaction using aziridine groups.

Examples of polyether groups containing impression materials are given in U.S. Pat. No. 5,569,691, US 2004/0146713 A1 and US 2006/0069180. Commercially available materials are sold e.g. under the brand Impregum™ (3M ESPE).

By "derivative" is meant a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. A derivative of a certain compound comprises the chemical structure of that compound, but may contain other side groups or moieties.

The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

"Room temperature curable" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

A "dental composition" or a "composition for dental use" or a "composition to be used in the dental field" is any composition which can be used in the dental field. In this respect the composition should not be detrimental to the patients' health and thus free of hazardous and toxic components being able to migrate out of the composition.

Examples of dental compositions include permanent and temporary crown and bridge materials, artificial crowns, anterior or posterior filling materials, adhesives, mill blanks, lab materials and orthodontic devices.

Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health.

Dental compositions are typically provided to the practitioner in comparable small volumes, that is volumes in the range from about 0.1 to about 500 ml or from about 0.5 to about 100 ml or from about 1 to about 50 ml. Thus, the storage volume of useful packaging devices is within these ranges.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is typically carried out by placing a viscous material into the mouth in a customised or stock tray. The material then sets to become an elastic solid, and when removed from the mouth retains the shape of the teeth and gingiva.

A "dental impression material" is a material used for making impressions of the tooth structure. A dental impression material is usually applied on a dental impression tray. A dental impression material can be based on different chemical substances and crosslink by various chemical reactions. Common materials used for dental impressions include alginate, agar, polyethers including aziridine substituted polyether materials as well as silicones, both condensation-cured silicones and addition-cured silicones including polyvinyl siloxanes (so-called VPS materials).

The term "dental impression materials" comprises precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE under the trademarks or Vestogum™.

A "putty like dental impression material" is a kneadable dental impression material having a consistency of 35 mm or below according to ISO 4823.

A "dental retraction material" is a material intended to be placed in the gingival sulcus, that is, the natural space between the hard dental tissue (i.e. tooth structure) and the gum tissue that surrounds the hard dental tissue. Once placed in the gingival sulcus, the dental retraction material will exert pressure on the surrounding tissue resulting in a widening of the gingival sulcus to enable the practitioner to get a more precise impression of the dental situation below the gum line during a dental impression process. Like a dental impression material, a dental retraction material is removed from the mouth of the patient after use.

The term "automixer-suitable material" relates to a multi-component material which can be dispensed, for example, from a two-component disposable cartridge through a static mixer, e.g., of SulzerMixpac Company (U.S. Pat. No. 5,464,131, US 2001/0004082) or from tubular film bags in dual-chamber reusable cartridges through a dynamic mixer, e.g., in the "Pentamix™", "Pentamix™ 2" and "Pentamix™ 3" devices of 3M ESPE Company (cf. U.S. Pat. Nos. 5,286,105 and 5,249,862).

The term "dental tissue" includes the hard tooth substance (enamel and dentin), the gingival region (soft dental tissue) surrounding the hard tooth substance and hard tooth substance bearing orthodontic appliances.

A "temporary crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to 6 days), a few weeks (1 to 4 weeks) or a few months (1 to 6 month).

A "surfactant" is an agent imparting wettability to a material, that is making the material more wettable compared to a material not containing a surfactant. The wettabilty can be determined by the water contact angle which can be measured using e.g. a goniometer DSA 10 (Kruss). A low water contact angle indicates a better wettability.

"Molecular weight" in the context of the invention and if not otherwise indicated always means number average molecular weight ($M_n$). The molecular weight (Mn) of the polymerizable compound before setting can be determined using nuclear magnetic resonance spectroscopy (end-group determination). In this respect proton ($^1$H) NMR techniques are employed to estimate the molecular weight of the precursor of the prepolymer. Integrated signals of the terminal —$CH_2$— groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

"Ambient conditions" within the meaning of the invention mean the conditions which the inventive solution is usually subjected to during storage and handling. Ambient conditions may for example: be a pressure of 900 to 1100 mbar, a temperature of −10 to 60° C. and a relative humidity of 10 to 100%. In the laboratory ambient conditions are adjusted to 23° C. and 1013 mbar.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than 1 wt.-% or less than 0.1 wt.-% or less than 0.01 wt.-% with respect to the whole composition. Ideally the composition does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims.

Also herein, the recitations of numerical ranges by endpoints include all numbers subsumed within that range (e.g., 1 to 5 includes 1, 1.5, 2, 2.75, 3, 3.80, 4.5, etc.).

"Comprise" includes the terms "contain", "essentially consists of" and "consists of".

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of properties used in the specification and claims are to be understood as being modified in all instances by the term "about". Any numerical value, however, inherently may contain certain errors necessarily resulting from the standard deviations found in their respective testing measurements.

Unless described otherwise, "wt.-%" refers to the weight of the composition obtained when combining the compositions of Part A and Part B of the kit of parts, which is also referred to as "whole composition".

"Water-adsorbing component" means a component being able to reversible adsorb water without undergoing a chemical reaction with water.

A "water-soluble component" is a component which can be dissolved in water at 23° C. and is able to dissociate in its ions, if present, like sodium chloride. The dissolving of the water-soluble component can typically be accomplished within a reasonable period of time; e.g. 1 g of the component dissolves with 100 ml of water if stirred for 10 min at 23° C.

DETAILED DESCRIPTION OF THE INVENTION

Figure 1:
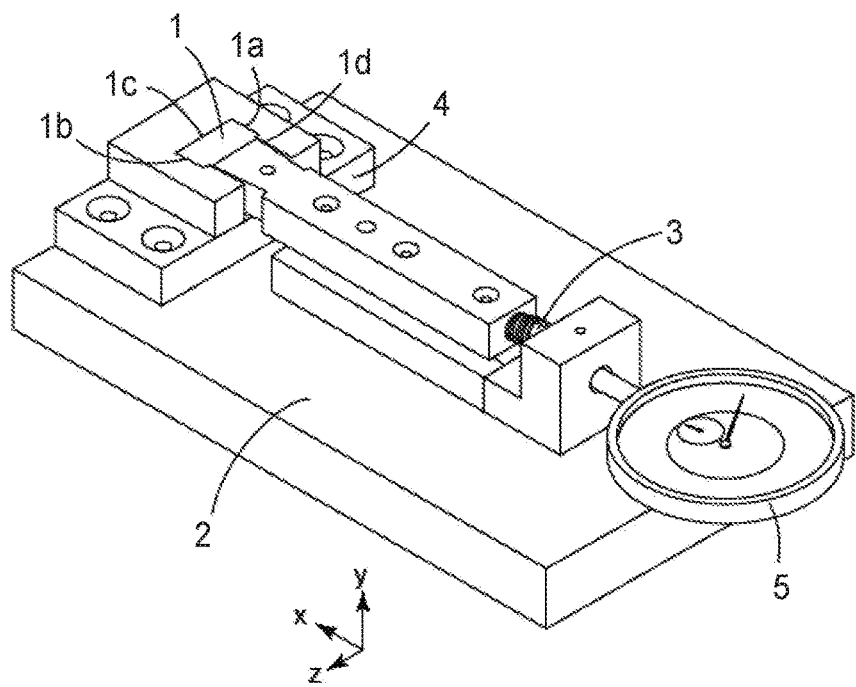
FIG. 1 shows a device suitable to measure the residual gap behavior of samples of hardenable compositions.

The means, in particular the kit of parts, described in the present text and the resulting composition are suitable to address at least some of the above issues.

The Base Paste described in the present text contains a cationically hardenable compound. Such a compound is already used in commercially available dental impression materials.

Thus, a dental retraction material obtained by combining the Base Paste and the Catalyst Paste has a very similar chemical composition compared to existing dental impression materials and can therefore be combined with those materials, if desired. This will reduce the number of steps to be taken for obtaining a dental impression being able to also record the details of the surface of hard dental tissue beyond the gumline.

Further, the kit of parts described in the present text allows for the provision of a hardenable composition having a sufficiently low viscosity for an easy application into the sulcus and a sufficiently high consistency for keeping the sulcus open.

It was found that the hardenable compositions obtained by mixing the Base Paste and the Catalyst Paste containing a water-adsorbing component and water shows a remarkable thickening effect as soon as the Base Paste and Catalyst Paste are mixed.

This effect is in particular advantageous as it helps to provide a hardenable composition for use as dental retraction material being able to remain in the sulcus during the hardening process and being able to withstand the pressure resulting from the surrounding dental tissue.

Besides this advantageous effect, the hardenable composition shows a sufficiently low viscosity before hardening. This facilitates an easy application of the composition into the sulcus, e.g. by using a syringe.

Surprisingly and despite the increased viscosity, the obtained composition is still able to flow and record the details of a dental preparation margin before it finally sets by a crosslinking reaction.

The presence of water in the composition may contribute to additional benefits.

E.g. it facilitates the use of a water-soluble starter component, as this kind of starter has to be dissolved in water to become effective.

A further benefit can be seen in that the presence of water also facilitates an easily introduction of other water-soluble components, e.g. components having an astringent property like salts of aluminum and/or iron. Adding astringents is sometimes desired to stop bleeding of the dental tissue. Bleeding of tissue may negatively influence the whole dental impression process.

The consistency of Base Paste (B) of the kit of parts described in the present text is typically equal or less than 28 mm, if determined according to ISO 4823.

The consistency of Catalyst Paste (C) of the kit of parts described in the present text is typically equal or less than 28 mm, if determined according to ISO 4823.

The composition obtained by mixing the Base Paste (B) and the Catalyst Paste (C) described in the present text fulfils typically at least one or more, sometimes all of the following parameters:

having a consistency being equal or less than 26 mm, if determined according to ISO 4823;
hardening within 15 min within a temperature range from 20 to 40° C. to a rubber elastic mass;
Shore hardness A according to DIN 53505 from 40 to 90 after 24 h;
showing a residual gap of more than 2.0 mm, preferably at least 3.0 mm, most preferred at least 4.0 mm, if determined according to the measurement described in the examples section.

The nature and structure of the cationically hardenable compound (Component A) is not particularly limited unless the desired result cannot be achieved.

The cationically hardenable compound according to component (A) typically comprises a backbone and at least one or two reactive functional group(s).

The backbone of the cationically hardenable compound typically comprises moieties selected from polyether, polyester, polyurethane, silicone, polyalkylene, polystyrol, polysulfide and combinations thereof.

In the dental field a polyether moieties containing backbone can be preferred. Those groups typically also improve the hydrophilic properties of the composition.

According to one embodiment, the cationically hardenable compound includes a polyether group containing hardenable prepolymer as component (A) or part of component (A), that is, a prepolymer comprising a polyether group(s) and reactive moieties which upon addition of a suitable catalyst or initiator can react with each other and thus form a polymeric network.

The molecular weight (Mn) of the polyether group(s) containing prepolymer is typically in a range from 150 to 20,000 g/mol, or in the range from 250 to 10,000 g/mol, determined e.g. with GPC methods know to the person skilled in the art.

Suitable polyethers or polyether groups, which can be used, include those which meet the requirements in terms of material properties with regard to the preferred use as dental materials.

Appropriate polyethers or polyether groups can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

The dental composition comprises at least a cationically hardenable compound having at least 1 aziridine moiety or more, if desired, e.g. at least 2 or 3 or 4 or 5 or 6 aziridine moieties. Using a cationically hardenable compound with at least 2 azirdine moieties can be preferred to ensure a sufficient crosslinking.

According to another embodiment, the cationically hardenable compound comprises on average at least 2 aziridine moieties.

The term "on average" is to be interpreted such in the context of the present text that a mixture of a large number of compounds may comprise both compounds having less than 2 aziridino groups and also compounds having more than 2 aziridine groups although, when seen over the entirety of the compounds of component (A), the average functionality of all molecules is, with respect to aziridine groups, 2 or more.

All mentioned types of polyaddition or polycondensation products can be provided with aziridine groups by means of any desired subsequent reactions known to the person skilled in the art. For example, it is possible first to introduce, into an appropriate polymer, substituents which are in turn capable of reacting with suitable aziridine derivatives.

It is also possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised.

Suitable possible methods for providing the polymers with aziridine groups are mentioned, e.g., in U.S. Pat. No. 3,453,242.

Suitable polymers carry the aziridine groups terminally or laterally, or terminally and laterally, but preferably terminally.

The aziridine groups containing compound typically have a dynamic viscosity 11 of from 10 to 500 Pa*s, especially from 15 to 300 Pa*s. A preferred viscosity range is from 20 to 180 Pa*s at 23° C.

The aziridine equivalent is typically from 250 to 25,000 g/equivalent, especially from 400 to 10,000 g/equivalent. The term "aziridine equivalent" is defined as (molecular mass of the molecule)/(number of aziridine groups present in the molecule).

Using compounds having such an aziridine equivalent weight may facilitate the provision of rubber-like or elastomeric materials (after hardening). Compounds having an aziridine equivalent weight outside this range might either be too hard or brittle or too soft, e.g. do not have the desired Shore hardness or tensile strength.

The cationically hardenable compound which can be used may comprise only one type of aziridine group containing polymer. It is, however likewise possible for the cationically hardenable compound to comprise two or more different types of aziridine polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

Reactive side groups which pending from or attached to the backbone of the prepolymer include those characterized by the following formula (I)

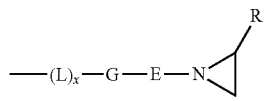

(I)

wherein

R represents H, $C_1$-$C_{12}$ alkyl, $C_2$-$C_{12}$ alkenyl, $C_2$-$C_{12}$ alkinyl, $C_7$-$C_{15}$ alkylaryl, $C_7$-$C_{15}$ arylalkyl, $C_3$-$C_{12}$ cycloalkyl, and wherein hydrogen atoms may be replaced by Cl or F and/or wherein up to five carbon atoms may be replaced by atoms or group of atoms selected from O, CO, N, S, E represents a $C_1$-$C_{18}$ branched or unbranched hydrocarbon chain wherein up to five carbon atoms may be replaced by atoms or group of atoms selected from O, CO, N, S, G represents a group selected from C(O)O, C(O)NR, C(O), C(O)C(O), C(O)($CH_2$)$_m$C(O) with m=1 to 10, C(S)NR, $CH_2$, L represents O, S, NR with x=0 or 1.

It can be preferred, if the cationically hardenable compound has a linear molecular structure. Thus, the cationically hardenable compound may typically comprise a linear backbone, which is typically end-capped with aziridine groups. Usually, there are no side chains, especially cationically hardenable side chains pending from the backbone.

The cationically hardenable compound is typically present in an amount, which allows the formation of a sufficiently crosslinked network, in order to fulfil the practitioners needs.

By varying the amount of the cationically hardenable compound, e.g. the viscosity and the hardness of the cured composition can be adjusted.

If the amount of the cationically hardenable compound is too low, the resulting composition might not cure within the desirable period of time or might show not desirable mechanical properties.

If the amount of the cationically hardenable compound is too high, the resulting composition might be too viscous.

If desired, besides the cationically curable compound containing at least two aziridine groups, further curable compounds can be present being different from the cationically hardenable compound described above.

Thus, blends of various cationically polymerizable resins are also contemplated in this invention. Examples of such blends include two or more weight average molecular weight distributions of resin-containing compounds, such as low molecular weight (below 200), intermediate molecular weight (200 to 10,000) and higher molecular weight (above 10,000).

Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

According to one embodiment, the cationically curable component is characterized by at least one of the following features:

Component A is typically present in the following amounts:

Lower amount: at least 5 or 12 or 15 wt.-%;
Upper amount: at most 90 or 80 or 70 wt.-%;
Range: from 5 to 90 or from 12 to 80 or from 15 to 70 wt.-%, wt.-% with respect to the weight of the whole composition.

The Catalyst Paste (C) of the kit of parts described in the present text contains a starter component as Component B.

The nature and structure of the starter component is not particularly limited, either unless the desired result cannot be achieved.

According to one embodiment, the starter component is a component which is water-soluble.

As mentioned above, using a water-soluble starter component can be beneficial, as the starter component will start to dissolve upon contact with water being present in the mixed composition and thus become more effective. There is no need for adding a further dissolvent for dissolving a water-soluble starter component.

According to one embodiment, the starter component is selected from Lewis acids or Broensted acids or precursors of Lewis acids which can be activated by radiation to produce a Lewis acid. In principle both organic and inorganic acids can be used. The starter component is present in the Catalyst Paste.

However, if the starter component is part of a starter or initiator system, the components of that starter or initiator system may be distributed among the Catalyst Paste and Base Paste of the kit of parts described in the present text. That is, in addition to the starter component being present in the Catalyst Paste, a further different starter component may be present in the Base Paste.

Specific examples of Broensted and Lewis acids, which can be used, include sulfonic acids, phosphonic acids, phosphoric acids, carboxylic acids, antimonic acids, boric acids and mixtures and salts thereof.

Particular useful initiators include sulfonium salts, especially alkyl sulfonium salts or sulfonium salts derived from glutaconic acid. Those and others are described e.g. in WO 2007/016295 (Klettke et al.) or U.S. Pat. No. 4,167,618 (Schmitt et al.). The content of these documents as regards initiators is explicitly mentioned and herewith incorporated by reference.

Suitable sulfonium acids and salts thereof include 4-toluenesulphonic acid, 4-phenolsulphonic acid, 4-bromobenzenesulphonic acid, 4-chlorobenzenesulphonic acid, benzenesulphonic acid, alkylbenzenesulphonic acids, in particular dodecylbenzenesulphonic acid, naphthalene-2-sulphonic acid and alkanesulphonic acids.

Other starters which can be used include strong acids such as hexafluoroantimonic acid, hexafluorophosphoric acid or tetrafluoroboric acid.

The use of phosphonic acids such as vinylphosphonic acid and propylphosphonic acid is also possible.

Polymeric acids such as polyvinylphosphonic acid, polyacrylic acid, copolymeric acids, prepared from maleic anhydride with other monomers can also be used, if desired.

Furthermore, saturated and unsaturated carboxylic acids such as propionic acid, succinic acid, tartaric acid, trimellitic acid, benzoic acid, phenylacetic acid, citric acid, maleic acid, adipinic acid, o-chlorobenzoic acid or reaction products of polyvalent alcohols and acid anhydrides such as maleic anhydride and succinic anhydride can also be used.

Those and other starters are described e.g. in US 2003/153726 (Eckhardt et al.). The content of this document as regards initiators is explicitly mentioned and herewith incorporated by reference.

The starter component being present in the Catalyst Paste (Component B) and being selected from Broensted or Lewis acids is typically present in the following amounts:
  Lower amount: at least 1 or 2 or 3 wt.-%;
  Upper amount: at most 30 or 20 or 10 wt.-%;
  Range: from 1 to 30 or from 2 to 20 or from 3 to 10 wt.-%;
wt.-% with respect to the weight of the whole composition.

If desired, the acids described above can be used in combination with one or more antacid-acting components.

Suitable antacid-acting components which can be used include oxides, hydroxides, carbonates and carboxylates of the elements aluminum, chromium, copper, germanium, manganese, lead, antimony, tin, tellurium, titanium and zinc, with aluminum and zinc being sometimes preferred.

In particular, the addition of zinc components such as zinc hydroxide, zinc oxide, zinc carbonate or mixtures of these components can be advantageous, e.g. for improving the storage stability of the composition, e.g. by reducing corrosion of the packaging material during storage of the composition.

With respect to certain compositions it was also found that adding in particular antacid-acting components containing Zn, the mechanical properties of the hardened composition can be improved.

If an antacid-acting component is added, the ratio between starter component (B) and the antacid-acting component is typically within a range from 0.5 to 2.0 or from 0.7 to 1.2 antacid-acting equivalents to one acid equivalent for starter component (B).

According to another embodiment, the starter according to component (B) is a radiation sensitive starter.

This starter is typically able to produce cations (e.g. including $H^+$) when exposed to radiation. Such a radiation sensitive starter, it is sometimes characterized as a latent Lewis acid source.

According to one embodiment, the radiation sensitive starter can be characterized by at least one or more of the following features:
  Molecular weight: being in a range from 350 to 2000 or from 400 to 1400,
  Reduction potential E1/2red (On+) of the onium salt: at least $-1.1$ Volt vs. SCE (Standard calomel electrode), or at least $-0.5$ Volt vs. SCE or at least $-0.3$ Volt vs. SCE.

Radiation sensitive starters which were found to be useful include onium salts, ferrocenium salts and mixtures thereof as long as they are radiation sensitive.

In this respect it should be noted that not all onium salts are radiation sensitive. E.g. the sulfonium salts described in U.S. Pat. No. 4,167,618, US 2005/200585, US 2006/106127 are not radiation sensitive. Those salts do not generate reactive species upon exposure to radiation with a wavelength in the range from 250 to 1,000 nm or within the spectrum visible to the human eye.

A particularly useful class of radiation sensitive starters include onium salts, especially iodonium salts or sulfonium containing low or non-coordinating anions.

Low or non-coordinating anions include $BF_4^-$, $PF_6^-$, $SbF_6^-$, $AsF_6^-$, $SbF_5OH^-$, $B(C_6F_5)_4^-$, $B(C_6(CF_3)_5)_4^-$, $B(C_6H_2(CF_3)_3)_4^-$.

Sulfonium salts which can be used include those bearing two or three aryl groups (including C1 to C8 substituted aryl and phenyl) attached to the sulfonium ion. Sulfonium salts, where the sulfonium ion bears an alkyl group are not useful, as those are typically not radiation sensitive.

Particularly, diaryliodonium salt(s) were found to be useful.

It can be advantageous, if the iodonium salt is soluble in the composition and preferably is shelf-stable, meaning it does not spontaneously promote polymerization when dissolved therein in the presence of the visible light sensitizer and the electron donor compound or without these additional components.

Accordingly, selection of a particular iodonium salt may depend to some extent upon the particular resin, and the optionally present visible light sensitizer and/or electron donor.

Suitable iodonium salts are described in U.S. Pat. Nos. 3,729,313, 3,741,769, 3,808,006, 4,250,053 and 4,394,403. The iodonium salt can be a simple salt, containing an anion such as $Cl^-$, $Br^-$, $I^-$ or $C_2H_5SO_3^-$; or a metal complex salt containing an antimonate, arsenate, phosphate or borate such as SbF$_5$OH$^-$ or AsF$_6^-$. Combinations of iodonium salts can be used if desired.

The diaryliodonium compounds may have the following structure (II):

$$[((R1)_aAr1)\text{-}I\text{—}(Ar2(R2)_b)]^+Y^- \quad (II)$$

with Ar1 and Ar2 being independently of each other substituted or unsubstituted, fused or non-fused aromatic systems having 4 to 20 C atoms, including, for example, phenyl, tolyl, cumyl, anisyl, chlorophenyl, nitrophenyl, naphthyl, thienyl, furanyl and pyrazolyl, wherein R1 and R2 are identical or different and independently of each other denote an H atom, an aliphatic radical having 1 to 19, preferably 1 to 9 C atoms, it being possible for one or more C atoms to be replaced by O, C=O, O(C=O), F, Cl, Br, SiR3$_3$ and/or NR3$_2$ wherein R3 is an aliphatic radical having 1 to 7 C atoms, in which one or more C atoms can be replaced by O, C=O and/or O(C=O), and a and b independently of each other can be 1 to 5. The aromatics Ar1 and Ar2 can be bonded to one another via R1 and/or R2.

The counter-anion Y$^-$ is typically an anion of low nucleophilicity having the following structure (III):

$$K_xL_y \quad (III)$$

wherein K is an element of main group III, V or VII, such as, for example, B, Al, P, Sb, As or I, and x can assume numerical values from 1 to 4, L independently of one another denotes aromatic, aliphatic, araliphatic or cycloaliphatic radicals having 1-25 C atoms, in which one or more C atoms can be replaced by F, Cl, Br or I, and y can assume numerical values from 0 to 6. Preferred radicals L are pentafluorophenyl, tetrafluorophenyl, trifluorophenyl, fluorophenyl, phenyl, 4-trifluoromethyl phenyl, 3,5-bis (trifluoromethyl)phenyl, 2,4,6-tris(trifluoromethyl)-phenyl, fluorine and iodine. Particularly preferred counter-ions Y$^-$ are PF6$^-$, SbF6$^-$ and B(C$_6$F$_5$)$_4^-$.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluoro-phosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl) iodonium hexafluorophosphate; di(4-bromophenyl) iodonium hexafluorophosphate; di(4-methoxyphenyl) iodonium hexafluorophosphate; di(3-carboxyphenyl) iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate.

Of the aromatic iodonium complex salts which are suitable for use in the compositions of the invention diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate, and 4-(1-methylethyl)phenyl 4-methylphenyliodonium tetrakis(pentafluorophenyl)borate are among the preferred salts. These salts are preferred because, in general, they promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate). Thus, for example, the complex salt diphenyliodonium tetrafluoroborate can be prepared by the addition at 60° C. of an aqueous solution containing 29.2 g silver fluoroborate, 2 g fluoroboric acid, and 0.5 g phosphorous acid in 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acetate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is stirred for an additional four hours at 0° to 5° C. and at room temperature (25° C.) for 48 hours and treated with 300 ml of diethyl ether. On concentration, crude diphenyliodonium bisulfate precipitates and may be purified by recrystallization if desired.

Besides onium salts also ferrocenium salts were found to be useful.

Ferrocenium salts which can be used include those represented by the following formula (IV):

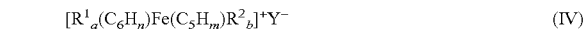

$$[R^1{}_a(C_6H_n)Fe(C_5H_m)R^2{}_b]^+Y^- \quad (IV)$$

with n=1,2,3,4,5; m=1,2,3,4; a=1,2,3,4,5; b=1,2,3,4; n+a=6; m+b=5;
R$^1$=H, C1 to C6 alkyl; R$^2$=H, C1 to C6 alkyl; Y=as defined above.

Specific examples for ferrocenium salts which can be used include eta-6-Cumol eta-5-cyclopentadienyl iron-hexafluorophosphate, eta-6-Cumol eta-5-cyclopentadienyl iron-hexafluoroantimonat, eta-6-Cumol eta-5-cyclopentadienyl iron-tetrafluorborat. Cumol or cumene has the formula C$_6$H$_5$CH(CH$_3$)$_2$.

The molar ratio between the starter and the cationically hardenable compound includes ranges from 1.0:0.1 to 1.0:20.0, or from 1.0:0.5 to 1.0:10.0, or from 1.0:0.8 to 1.0:30. As the starter does not only act as a catalyst but chemically react—to a certain extend—with the hardenable composition, a sufficient amount of initiator should be present.

The amount of the starter to be used is not particularly limited, unless the desired curing reaction cannot be achieved.

If the starter component being present in the Catalyst Paste (Component B) is a radiation sensitive starter, the starter is typically present in the following amounts:
Lower amount: at least 1 or 2 or 3 wt.-%;
Upper amount: at most 30 or 20 or 10 wt.-%;
Range: from 1 to 30 or from 2 to 20 or from 3 to 10 wt.-%;
wt.-% with respect to the weight of the whole composition.

It can be beneficial, if the cationically hardenable composition can be cured by using visible light, that is, with radiation having a wavelength in the range from 380 to 800 nm or from 400 to 500 nm.

In this case, it is recommended that a sensitizer, especially a visible light sensitzer is present.

If a sensitizer is present, it can be in only one or in both pastes of the kit of parts described in the present text.

A "sensitizer" is defined as a compound or a combination of compounds which are able to absorb the radiation in the emitted wavelength or in a region of the emitted wavelength and to generate the initiating species of the polymerization reaction.

According to one embodiment, the sensitizer may have a molecular weight: being in a range from 50 to 1000 or from 100 to 800.

The sensitizer should be partly, essentially or completely soluble in the photopolymerizable composition, free of functionalities that would substantially interfere with the cationic polymerization process, and capable of light absorption somewhere within the range of wavelengths between 400 and 1000 nanometers (nm). Preferred visible light sensitizers contain one or more carbonyl functional groups.

Suitable visible light sensitizers may include compounds in the following categories: ketones, coumarin dyes (e.g., ketocoumarins), xanthene dyes, fluorone dyes, fluorescein dyes, aminoketone dyes, and p-substituted aminostyryl ketone compounds. Ketones (e.g., monoketones or alpha-diketones), coumarin dyes (e.g., ketocoumarins), xanthene dyes, fluorone dyes, and fluorescein dyes are particularly preferred visible light sensitizers for use in the invention. For applications requiring deep cure, it is preferred to employ sensitizers having an extinction coefficient below 1000 lmole$^{-1}$ cm$^{-1}$, more preferably or below 100 lmole$^{-1}$ cm$^{-1}$, at the desired wavelength of irradiation for photopolymerization.

The alpha-diketones are an example of a class of visible light sensitizers having this property, and are particularly preferred for dental applications.

By way of example, a preferred class of ketone visible light sensitizers has the formula (V):

ACO(X)$_b$B  (V)

where X is CO or CR$^1$R$^2$ where R$^1$ and R$^2$ can be the same or different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable I-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, 1-phenyl-1,2-propanedione, and the like.

Examples of particularly preferred visible light sensitizers include the alpha-diketones: camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione. Of these, camphorquinone is the most preferred visible light sensitizer.

Examples of preferred fluorone dyes include, but are not limited to, fluorescein, 4'5'-dibromofluorescein, erythrosin B, ethyl eosin, eosin Y, and erythrosin, yellowish blend.

The molar ratio between the sensitizer and the starter includes ranges from 1.0:0.1 to 1.0:20.0, or from 1.0:0.5 to 1.0:10.0, or from 1.0:0.8 to 1.0:30.

The amount of the sensitizer to be used is not particularly limited, unless the desired curing reaction cannot be achieved.

The starter or initiator system used for hardening the composition may also comprise an electron donor compound.

Adding an electron donor compound can be beneficial, if the hardenable composition should be hardened using visible light.

If an electron donor compound is present, it can be in only one or in both pastes of the kit of parts described in the present text.

A wide variety of electron donor compounds can be employed, and generally are capable of increasing the speed of polymerization and/or the depth of polymerization of the inventive composition when exposed to visible light of the desired wavelength, as compared to the same composition but excluding the electron donor compound.

Preferred electron donor compounds possess one or more (and more preferably several if not all) of the following properties:

(a) they are at least partly soluble in a polymerizable or hardenable composition;

(b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer;

(c) they have an oxidation potential ($E_{ox}$) greater than 0 but less than that of 1,4-dimethoxybenzene when measured versus a saturated calomel electrode (SCE);

(d) they yield a photoinitiator system that has a photoinduced potential less than that of 3-dimethylaminobenzoic acid in a standard solution of 2.9×10$^{-5}$ moles/g diphenyl iodonium hexafluoroantimonate and 1.5×10$^{-5}$ moles/g camphorquinone in 2-butanone;

(e) they impart not more than a minimal amount of objectionable colour to the polymerized resin;

(f) they can be used in a lower effective concentration than other polymerization aids. Other factors that may influence the selection of the electron donor compound for a particular composition include the cationically polymerizable resin, the iodonium salt, and the visible light sensitizer that have been chosen, as well as the shelf stability of the cationically polymerizable composition.

A wide variety of electron donor compounds can be used including biphenylene(s), anthracene(s), aromatic tertiary amine(s), aromatic ether(s), mixtures, derivatives and combinations thereof.

One class of electron donor compounds which can be used are compounds containing a biphenylene structure, including biphenylenes bearing alkyl groups.

In a preferred embodiment the alkyl groups pending on the biphenylene ring structure are arranged symmetrically.

The alkyl substituents are preferably at the positions 2, 3, 6, and 7. In a further embodiment there are not more than 2 substituents at the positions 2 and 6 or 2 and 7. Preferably, the alkyl substituents are independently selected from methyl groups or tert-butyl groups. The biphenylene structure typically does not comprise alkoxy groups like e.g. methoxy groups, being directly attached onto the biphenylene structure.

More specifically, electron donor compounds comprising the structure (VI) shown below may be employed.

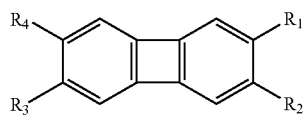

(VI)

wherein each of $R_1$ to $R_4$ is independently selected from H, or alkyl groups, wherein the R-group substituents may also cooperate to form a cycloalkyl ring. Preferred R-group substituents include methyl, ethyl, iso-propy, n-propyl, and tert-butyl groups, with the methyl and tert-butyl groups being most preferred.

More specifically, according to a preferred embodiment the electron donor compound of the invention can be characterized by at least one of the following features:
a. The biphenylene compound bears at least one, two or three but not more than four alkyl (e.g. C1 to C4) groups.
b. The substituted biphenylene compound is symmetric (reflection and/or rotation).
c. The biphenylene compound does not contain alkoxy groups directly attached onto the biphenylene structure.
d. The biphenylene compound has a molecular weight in the range of 180 to 380.

The combination of features a, c and d or b, c and d can be preferred.

Another class of electron donor compounds which can be used are compounds containing an anthracene structure.

The anthracene may be, for example, an unsubstituted anthracene or an alkyl or alkoxy substituted anthracene, such as 2-ethyl-9,10-dimethoxyanthracene (EDMOA), 2,6-di-tert-butylanthracene, 9,10-diethoxyanthracene, 1,4-dimethoxyanthracene or 9,10-dimethylanthracene. If desired, mixtures of anthracenes can be used.

In another embodiment, a combination of two or more substituted anthracenes, wherein one of the anthracenes is an alkoxy substituted anthracene (e.g., EDMOA) and the other anthracene is an alkyl, phenyl or alkoxy substituted anthracene.

It is also possible to use alone or in combination anthacenes comprising the structure (VII)

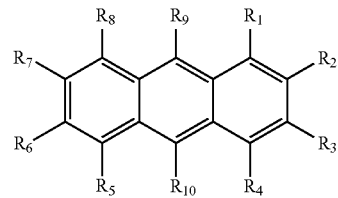

(VII)

wherein each of $R_1$ to $R_{10}$ is independently selected from H, alkyl (e.g. $C_1$ to $C_{10}$), phenyl or alkoxy groups (e.g. $C_1$ to $C_{10}$), provided that at least one of $R_1$ to $R_{10}$ is not H.

Preferred R-group substituents are methyl, ethyl, propyl, butyl, tert-butyl, methoxy, and ethoxy.

Particularly useful anthracene-based compounds include: 2-ethyl-9,10-dimethoxyanthracene (EDMOA), 9,10-dimethylanthracene, 9,10-diethoxyanthracene, 1,4-dimethoxyanthracene, 9-methylanthracene, 2-ethylanthracene, 2-tert-butylanthracene, 2,6-di-tert-butylanthracene, 9,10-diphenyl-2,6-di-tert-butylanthracene, 1-amino anthracene, 2-amino anthracene and combinations thereof. All of these compounds with the exception of the 2,6-di-tert-butylanthracene derivatives are available from Sigma-Aldrich, St. Louis, Mo.

Another class of electron donor compounds which can be used are compounds containing an aromatic tertiary amine structure as e.g. described in U.S. Pat. No. 6,084,004 and/or U.S. Pat. No. 6,043,295: (which is herewith incorporated by reference):

$$R^1R^2N\text{-Aryl-}R^3 \quad \text{(VIII)}$$

with $R^1$, $R^2$ and $R^3$ being identical or different and independently of one another selected from H, an aliphatic, aromatic or araliphatic radical having 1 to 19 or 1 to 7 carbon atoms, it being possible for one or more carbon atoms to be replaced by O, C=O, —O(C=O)—, wherein $R^1$ and $R^2$ together can from ring structures which are unsubstituted or substituted by aliphatic (C1-C19), cycloaliphatic, (C1-C20) heteroaromatic or fused aromatic radicals. Typical examples include dimethylaniline, diethylaniline, 4-dimethylaminobenzoic acid, ethyl 4-dimethylaminobenzoate, 3-dimethylaminobenzoic acid, 4dimethylaminobenzoin, 4-dimethylaminobenzaldehyde, and 4-dimethylaminobenzonitrile.

Another class of electron donor compounds which can be used are aryl alkyl polyether(s).

Useful compounds can be characterized by the following formula:

$$(R^4\text{—O})_n\text{-Aryl-O—}CHR^3_2 \quad \text{(IX)}$$

with n being 1 to 3, and $R^3$ and $R^4$ being independently H or $C_{1-18}$ alkyl that is optionally substituted by one or more halogen, —CN, —OH, —SH, $C_{1-18}$ alkoxy, $C_{1-18}$ alkythio, $C_{3-18}$ cycloalkyl, aryl, substituted aryl, —COOH, COOC$_{1-18}$ alkyl.

Typical examples include those mentioned in U.S. Pat. No. 6,043,295 (which is herewith incorporated by reference) and in particular 1,2,4-trimethyloxybenzene.

The amount of the electron donor compound which can be used is not particularly limited, unless the desired curing reaction cannot be achieved.

The nature and structure of the porous water-adsorbing component (Component C) is not particularly limited, either, unless the desired result cannot be achieved.

However, the water-adsorbing component need to be porous. Non-porous components were found to be not suitable.

Similarly, using porous components having a BET surface below 200 m²/g do not show the desired effect to an extend making the composition useful for keeping the sulcus of a tooth open for the desired period of time.

The water-adsorbing component can be present in either the Base Paste or the Catalyst Paste of the kit of parts described in the present text. According to a preferred embodiment, the water-adsorbing component is present in the Base Paste.

If desired, a mixture of different water-adsorbing components can be used.

The water-adsorbing component has to be kept separate from the water before the Base Paste and the Catalyst Paste are mixed.

Component C is typically present in the following amounts:
  Lower amount: at least 1 or 2 or 5 wt.-%;
  Upper amount: at most 60 or 40 or 20 wt.-%;
  Range: from 1 to 60 or from 2 to 40 or from 5 to 20 wt.-%;
wt.-% with respect to the weight of the whole composition.

The ratio of the porous water-adsorbing component being present in the one paste to water being present in the other paste being from 1.00:0.50 to 1.00:0.05 or from 1.00:0.50 to 1.00:0.25 or from 1.00:0.10 to 1.00:0.05 with respect to weight.

Using such a ration was found to be particularly useful to achieve the desired thickening effect when mixing the both pastes.

The porous water-adsorbing component typically has a BET surface of at least 200 or 300 or 400 m²/g or at least 450 m²/g.

Typical ranges for the BET surface of the water-adsorbing component are from 200 to 1,200 m²/g or from 300 to 1,100 m²/g or from 400 to 1,000 m²/g.

According to one embodiment, the porous water-adsorbing component is characterized by at least one or more of the following features:
  average pore diameter: below 100 nm or below 85 nm or below 50 or below 20 or below 10 or below 5 nm;
  average particle size: from 1 to 50 μm or from 2 to 40 μm;
  pH value: above 7 or above 8;
  being able to reversibly adsorb water.

Water-adsorbing components having an average pore diameter in the range from 0.3 nm to 50 nm or from 1 nm to 20 nm were found to be particularly useful as the resulting composition showed an even increased thickening effect, once Base Paste (B) and Catalyst Paste (C) are combined.

Thus, according to one embodiment, the water-adsorbing component can be characterized as a microporous material (average pore diameter of less than 2 nm) or mesoporous material (average pore diameter between 2 and 50 nm).

If the pH value of the porous water-adsorbing component is below 7, the shelf-life of the kit of parts may negatively be affected. Thus, using a basic porous water-adsorbing component, e.g. having a pH value above 8 was found to be particularly useful.

Suitable molecular sieves, zeolites and silica gel(s) are commercially available from e.g. Evonic company, Zeochem company or UOP company.

Examples of suitable water-adsorbing components are marketed under the trade designations Zeolite 3A, Zeolite 4A, Zeolite 5A, Zeolite 13X, Zeolite Y, Sipernat™, Purmol™ etc.

According to one embodiment, the porous water-adsorbing component is characterized by the formula $M^{n+}_{x/n}[(AlO_2)^-_x (SiO_2)_y]$, with n being 1 or 2, M being an alkaline or earth alkaline metal cation, y being from 1 to 150 with y/x being not below 1.

Water (Component D) can be present in either the Base Paste or the Catalyst Paste of the kit of parts described in the present text. According to a preferred embodiment, the water is present in the Catalyst Paste.

The water may also contribute to dissolve water soluble components being present in the composition like waters soluble starters or water soluble additives (e.g. astringents, if present).

Component D is typically present in the following amounts:
  Lower amount: at least 0.1 or 0.5 wt.-%;
  Upper amount: at most 10 or 5 or 2 wt.-%;
  Range: from 0.1 to 10 or from 0.1 to 5 or from 0.1 to 2 wt.-%;
wt.-% with respect to the weight of the whole composition.

The composition(s) described in the present text may also contain filler(s) as Component E.

A wide variety of inorganic, hydrophilic or hydrophobic fillers may be employed such as silicas, aluminas, magnesias, titanias, inorganic salts, metallic oxides, quartz, cristobalit, kaolin, talcum, feldspar, wollastonit, nephelinsyenit, silicates and glasses. It has been found to be possible to employ mixtures of silicone dioxides, such as a diatomaceous earth and/or fumed silica. Those filler are commercially available from companies like Degussa/Evonik or Wacker under the trade names Aerosil™, HDK-H, HDK 2050.

The following commercially available fillers were found to be particularly useful: quartz comprising amino-silane groups (e.g. Silbond™ 600 AST, Silbond™ 800 AST; Quarzwerke Frechen), wollastonite comprising amino-silane groups (e.g. Tremin™ 283-600 AST or Tremin™ 939-300 AST; Quarzwerke Frechen), quartz/kaolin mixture comprising amino-silane groups (e.g. Aktisil™ AM; Quarzwerke Frechen), quartz comprising epoxy groups (e.g. Silbond™ 600 EST, Silbond™ 800 EST; Quarzwerke Frechen) and quartz comprising trimethyl-silane groups (e.g. Silbond™ 800 RST).

More specifically, fillers which can be used include calcium silicate, diatomaceous earth, zirconium silicate, montmorillonite such as bentonite, barium sulphate, calcium carbonate, plaster, glass and plastic powder.

The sizes and surface areas of the foregoing materials can be adjusted to control the viscosity and thixotropicity of the resulting compositions.

A combination of reinforcing and non-reinforcing fillers sometimes even further improves the rheology of the un-cured composition and the elasticity of the cured composition.

Typical reinforcing fillers include fumed silica, carbon black and the like. They also can improve mechanical properties like tensile strength or tear strength, of the cured silicone composition.

Typical non-reinforcing fillers include precipitated silicas, diatomaceous earth, aluminas, magnesias, titanium dioxide, zirconium silicate and mixtures and combinations thereof.

If present, Component E is typically present in the following amounts:
  Lower amount: at least 1 or 5 or 10 wt.-%;
  Upper amount: at most 70 or 60 or 50 wt.-%;
  Range: from 1 to 70 or from 5 to 60 or from 10 to 50 wt.-%;
wt.-% with respect to the weight of the whole composition.

If the amount of the filler is too low, a desired Shore hardness might not be obtained.

If the amount of the filler is too high, the elasticity of the cured composition might negatively be affected and the viscosity of the un-cured composition might be too high. Moreover, the shelf life might negatively be influenced.

Besides surface-treated fillers, non-surface treated fillers can be added. A "non-surface treated filler" in the present context is a filler having a surface which has not been exposed to reactive substances resulting in a modification of the surface of the filler to make the filler more compatible with other components of the composition.

Filler component (E) may be present in either the Catalyst Paste (C) or the Base Paste (B) or in both pastes, Catalyst Paste (C) and Base Paste (B).

According to a further embodiment, the composition described in the present text can also comprise one or more additives as Component (F).

The dental compositions can contain suitable adjuvants such as accelerators, inhibitors or retarders, stabilizers, pigments, dyes, viscosity modifiers, surfactants and wetting aids, antioxidants, astringents and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include colorants like pigments, and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER.

Accelerators, which can be used include components having a bi- or polycyclic aromatic amine structure, especially a bi- or polycyclic aromatic tert. amin or a bi- or polycyclic aromatic like N,N-dialkyl (e.g. C1 to C12 or C1 to C6) amine. Specific examples include 1,8-bis(N,N-dimethylamino)-naphthaline and N,N-dimethyl-1-naphthylamine.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol, 4-methoxybenzylalcohol, 2,6-di-tert.-butyl-4-methylphenol ("Jonol"), 3-methoxyphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentyl-phenyl)-2H-benzotriazole, 2-hydroxy-4-n-octoxybenzophenone, 2-(2'-hydroxy-5'-methacryloxyethylphenyl)-2H-benzotriazole, phenothiazine, tocopherol, polyethylene imine, substituted pyridines (e.g. 2,6-di-tert.-butyl-4-methylpyridine) and HALS (hindered amine light stabilizers). Such adjuvants may optionally comprise reactive functionality so that they will be copolymerized with the resin.

All kinds of known and compatible softeners and rheology modifiers like non-reactive polymeric fluids or fats commonly used in commercialized impression materials can be added Preferred are those ingredients and additives that do not add unpleasant smell or taste. Compounds that have an unpleasant smell might be removed by thin film evaporation, if needed.

Typical plasticisers include, e.g., compounds of the ester type such as C12- to C15-alkyl lactates, ethyl or butyl esters of citric acid or of acetylcitric acid, phthalic acid esters of relatively long, branched alcohols such as bis(2-ethylhexyl) phthalate or phthalic acid polyester, C2- to C22-dialkyl esters of C2- to C6-dicarboxylic acids such as bis(2-ethylhexyl) adipate, dioctyl maleate, diisopropyl adipate, aromatic and aliphatic sulfonic acid esters such as C2- to C20-alkylsulfonic acid esters of phenol or of C1- to C22-alkanols or typical aromatic plasticisers such as polyphenyls in a wide viscosity range, including wax-like polyphenyls such as are obtainable, for example, from the Monsanto company, isomeric mixtures of C20 to C40 aromatic compounds, with preference being given to the use of mixtures of plasticisers of the ester type and aromatic type.

Liquids such as C12-C15 alkyl acetates, liquid derivatives of citric acid, esters of phthalic acid with branched alcohols like bis(2-ethylhexyl)phthalate or polymeric phthalates, C2-C18 bis(alkyl)esters of C2-C6 dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene sulfonic acid amide, typical aromatic diluters like poly phenyls, xylyl toluene, and dixylyl toluene can be used. Also low molecular weight alcohols that may contain more than one OH-function like propane-1,2-diol may be used. From the group of polymeric compounds, polypropylene glycols and its derivatives are sometimes preferred.

An example of a preferred plasticiser combination is a mixture of acetyl tributyl citrate and dibenzyltoluene.

Suitable diluting agent(s) usually do not contain reactive moieties like —SH or —COOH, primary or secondary amino groups, but may contain —OH. Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl) esters of $C_2$-$C_6$ dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, dibenzyl toluene, xylyl toluene, dixylyl toluene and polymeric compounds like polyethers, polyesters, polycarbonates, polytetrahydrofuranes, polyolefines can be used. Also low molecular weight alcohols that may contain more than one OH-function like propane-1,2, diol or carbonates like propylene carbonate may be used. From the group of polymeric compounds, polypropylene glycols and its derivatives are preferred.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in U.S. Pat. No. 6,395,801, to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illlipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopädie der industriellen Chemie", 4th edition, volume 11, p. 469.

Mixtures of naturally occurring fats, and also synthetically prepared fats such as Softisan™ 154 or Dynasan™ 118 (from Hüls Comp.) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula (XII):

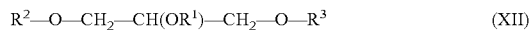

$$R^2-O-CH_2-CH(OR^1)-CH_2-O-R^3 \quad (XII)$$

in which $R^1$, $R^2$ and $R^3$ denote, each independently of the others, $C_{11}H_{23}CO$, $C_{13}H_{27}CO$, $C_{15}H_{31}CO$ or $C_{17}H_{35}CO$. Mixtures of such triacyl glycerides can also be used.

The curable composition may also include one or more surfactant(s), especially Si-containing surfactant(s) or mixture of Si-containing surfactants.

If surfactant(s) are present they are typically present in an amount sufficient and not detrimental to the desired effect or effects to be achieved.

Surfactants or hydrophilizing agents which can be employed can generally be chosen freely from all types of surfactants which improve the hydrophilicity of a polyether group containing polymer.

Preferably, the use of the surfactant should not negatively impact the material properties or curing behavior of the curable composition or at least not more than avoidable or tolerable.

Surfactant(s) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state).

In certain embodiments, the surfactant does not contain reactive groups so that it is not incorporated into the network of the hardenable composition.

Useful surfactants also include polyether carbosilanes of the general formula (XIII)

$$Q\text{-}P-(OC_nH_{2n})_x-OZ \quad (XIII)$$

in which Q stands for $R_3Si-$ or $R_3Si-(R'-SiR_2)_a-R'-SiR''_2-$, where every R in the molecule can be the same or different and stands for an aliphatic $C_1$-$C_{18}$, a cycloaliphatic $C_6$-$C_{12}$ or an aromatic $C_6$-$C_{12}$ hydrocarbon radical, which can optionally be substituted by halogen atoms, R' is a $C_1$-$C_{14}$ alkylene group, R" is R in the case of a≠0 or is R or R3SiR' in the case of a=0, and a=0-2; P stands for a $C_2$-$C_{18}$ alkylene group, preferably a $C_2$-$C_{14}$ alkylene group or A-R''', where A represents a $C_2$-$C_{18}$ alkylene group and R''' a functional group selected from: —NHC(O)—, —NHC(O)—$(CH_2)_{n-1}$—, —NHC(O)C(O)—, —NHC(O)$(CH_2)_v$C(O)—, —OC(O)—, —OC(O)—$(CH_2)_{n-1}$—, —OC(O)C(O)—, —OC(O)$(CH_2)_v$C(O)—, —OCH$_2$CH(OH)CH$_2$OC(O)$(CH_2)_{n-1}$—, —OCH$_2$CH(OH)CH$_2$OC(O)$(CH_2)_v$C(O)— with v=1-12; Z is H or stands for a $C_1$-$C_4$ alkyl radical or a $C_1$-$C_4$ acyl radical; x stands for a number from 1 to 200 and n stands for an average number from 1 to 6, preferably 1 to 4. Thus, the element —SiR''$_2$— can also comprise the substructure —Si(R)(R$_3$SiR')—.

Other surfactants which can be used, either alone or as a mixture of two or more thereof, can be found in U.S. Pat. No. 4,657,959 (Bryan et al.), col. 4, 1. 46 to col. 6. 1. 52 as well as in EP 0 231 420 B1 (Gribi et al.; also published as AU 6,857,087) p4, 1. 1 to p. 5, 1. 16 and in the examples.

U.S. Pat. Nos. 5,750,589, 4,657,959 and EP 0 231 420 B1 are expressly described and cited herein as a source of disclosure for compounds which can be used as component (E1) according to the invention.

Some of the surfactants, which can be used can be summarized under the following formula (XIV)

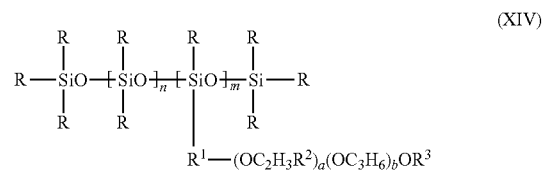

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is zero or one, m is one to five, a is five to 20 and b is 0.

Several of such ethoxylated surfactants are for example available from Momentive Performance Materials Inc. including "SILWET™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is zero or one, m is one or two, a is seven, and b is 0. Also possible is the use of MASIL™ SF19, as obtainable from Lubrizol performance products, Spartanburg, US.

Examples of useful non-ionic surfactants include those according to the formula (XV):

$$R^1-O-[CH_2CH_2O]_n-[R^2O]_m-R^3 \quad (XV)$$

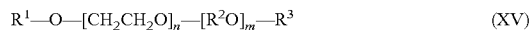

wherein $R^1$ represents hydrogen or an aromatic or aliphatic, linear or branched hydrocarbon group having 1-20 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is 10 or TRITON™ X 114 wherein the number of ethoxy units is 7 to 8.

Still further examples include those in which $R^1$ in the above formula represents an alkyl group of 4 to 20 carbon atoms, m is 0 and $R^3$ is hydrogen. An example thereof includes isotridecanol ethoxylated with 8 ethoxy groups and which is commercially available as GENAPOL™ X080 from Clariant GmbH.

Non-ionic surfactants according to the above formula with $R^1$ and $R^3$ representing a C1-C3 alkyl chain or hydrogen and in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

The inventive composition may also comprise in addition to other ingredients and surfactants, alone or in combination an F-containing component including those described in EP application number 09162681.2, especially those described on pages 21 to 27.

Astringent(s) which may be included comprise aluminium salts like aluminium sulfate, aluminium ammonium sulfated, aluminium chlorohydrated, aluminium acetate and mixtures thereof. Useful astringent(s) can also contain iron or manganese containing substances.

Incorporating an astringent may help to prevent or reduce the risk of bleeding during use or after removal of the composition from the mouth of a patient.

As the composition obtained when mixing the Base Paste and the Catalyst Paste contains water, the astringent will become even more effective as at least a part of the astringent will already be in its dissolved stage.

If present, the additive(s) are typically present in the following amounts:
Lower amount: at least 0.005 or 0.01 or 0.1 wt.-%;
Upper amount: at most 50 or 40 or 30 wt.-%;
Range: from 0.005 to 50 or from 0.01 to 40 or from 0.1 to 30 wt.-%;
wt.-% with respect to the weight of the whole composition.

If additive(s) are present, they are typically present in an amount sufficient and not detrimental to the desired effect or effects to be achieved.
Additive(s) (F) may be present in the Catalyst Paste (C) or the Base Paste (B) or in both pastes, Catalyst Paste (C) and Base Paste (B).

According to one embodiment, the composition obtained by combining the Base Paste and Catalyst Paste described in the present text comprising:
cationically hardenable compound having a backbone comprising polyether moieties and having at least two aziridino groups attached to the backbone, the cationically hardenable compound being present from 5 to 90 wt.-% or from 12 to 80 wt.-% or from 15 to 70 wt.-%;
starter component selected from Broensted, Lewis acids and precursors of Lewis acids which can be activated by radiation to produce a Lewis acid and being present from 1 to 30 wt.-% or from 2 to 20 wt.-% and being present from 3 to 10 wt.-%,
porous water-adsorbing component being present from 1 to 60 wt.-% or from 2 to 40 wt.-% or from 5 to 20 wt.-%,
water: from 0.1 to 10 wt.-% or from 0.1 to 5 wt.-%, and being present from 0.1 to 2 wt.-%,
an antacid acting compound selected from salts of Zn, Al or mixtures thereof, the antacid acting compound being present from 0.5 to 2.0 wt.-% or from 0.7 to 1.2 wt.-%;
wt.-% with respect to the weight of the whole composition.

The composition(s) described in the present text can be produced by a process comprising at least one mixing or compounding step of the individual component of the composition. Mixing or compounding can be accomplished by using a kneader, speedmixer or a dissolver.

The dental composition can be obtained by combining (including mixing and kneading) the individual components or compounds of the composition. If a radiation sensitive starter is used, the composition is typically prepared under "safe light" conditions.

Suitable inert solvents may be employed when formulating this mixture. Any solvent may be used which does not react appreciably with the components of the inventive compositions. Examples of suitable solvents include acetone, dichloromethane, acetonitrile, propylene carbonate, poly-THF and lactones (e.g. gamma-butyrolactone). A liquid material to be polymerized may be used as a solvent for another liquid or solid material to be polymerized. Solventless compositions can be prepared by simply dissolving the iodonium complex salt, sensitizer, and electron donor in the cationically polymerizable resin, with or without the use of mild heating to facilitate dissolution.

The individual components of the ternary photoinitiator system are provided in photopolymerizingly effective amounts (i.e., amounts effective to yield a photoinitiator system that can initiate photopolymerization of the cationically polymerizable resin or, more preferably, that can accelerate the rate of polymerization).

The composition described in the present text is provided in separate parts before use. This is beneficial for improving the storage stability and/or shelf life.

When used, the components of the compositions are mixed in the suitable amounts and applied using conventional techniques.

Providing a base paste and a catalyst paste with nearly equal viscosities may facilitate the mixing to obtain a homogeneous composition, especially if the mixing is done using a static mixing tip.

The volume ratios of catalyst paste and base paste can range from 10:1 to 1:10. Particularly preferred volume ratios of base paste to catalyst paste are from 1:1 to 10:1 or from 2:1 to 5:1 (e.g. 5 parts of base paste to 1 part of catalyst paste) or from 2:1 to 4:1.

The composition described in the present text is typically stored in a container until use. Depending on the initiator system chosen, various containers can be suitable.

A suitable capsule for storing the compositions described in the present text has typically a cylindrical housing with a front and a rear end and a nozzle. The rear end of the housing is usually sealed with a movable piston. The nozzle may have a shape to allow a dispensing of the composition into the sulcus of a tooth. Typically, the dental composition is dispensed out of the capsule or container using an applier having a movable plunger (e.g. an application device having the shape of a caulk gun).

If the composition is applied into the sulcus of a teeth (i.e. the region between gum and hard dental tissue), using a container with a nozzle as shown and described in WO 2009/151983 A2 can be beneficial due to its specific geometry.

Cartridges which can also be used are described e.g. in US 2007/0090079 or U.S. Pat. No. 5,918,772. Cartridges which can be used are commercially available from SulzerMixpac AG (Switzerland).

Other suitable devices can be found in WO 2005/016783 A1, WO 2007/047381, WO 2007/104037, and WO 2009/061884. If desired, the composition can also be stored in foil bags.

In practice, the composition (if provided as a two-component system) is syringed through a static or dynamic mixing device onto a surface or into an impression tray or onto the patients' teeth or tissue (including sulcus) and placed in the patients' mouth. The mixed pastes may also be applied using an applicator like an elastomer syringe.

If the dental composition contains a radiation sensitive starter, the radiation which can be used for starting the hardening reaction of the radiation curable inventive composition is not particularly limited. All kind of radiation can be used, which is sufficient in energy. The more energetic the radiation is, the less time is typically required to start the hardening reaction.

Radiation having a wavelength in the range from 250 to 1,000 nm or from 350 to 700 nm or from 400 to 500 nm was found to be useful.

In the dental and orthodontic area commercially polymerization lamps are sold under the trade name Elipar™ Freelight (3M ESPE).

If desired the composition can be cured at ambient temperature or a temperature which is typically present in the mouth of a patient (e.g. within a range from 15 to 40° C.) at ambient pressure (e.g. within a range from 850 to 1,100 hPa).

Depending on the thickness and transparency of the composition to be cured, radiation is typically applied for a time period ranging from a few seconds to a few minutes, e.g. from 1 s to 120 s or from 5 s to 60 s from 10 s to 40 s. The following combination of parameters was found to be particularly effective:
  Wavelength: from 400 to 500 nm.
  Duration: from 2 s to 2 min or from 10 s to 1 min or from 20 s to 40 s.
  Power: from 300 mW/cm$^2$ to 2500 mW/cm$^2$.

The exposure of the composition to radiation can be repeated, if desired.

The hardenable dental composition described in the present text is not only suitable as dental impression material but also as dental retraction material.

According to one embodiment, the dental composition is used as or for producing a dental retraction material.

The hardenable composition can not only be easily placed in the sulcus of a tooth, but also exerts sufficient pressure on the surrounding soft tissue having the result that the sulcus is widened. Due to its elastomeric properties in its cured stage, the composition can also be easily removed from the sulcus after hardening.

If used in the dental field, curing is preferably carried out at a temperature below 50° C. and preferably below 40° C.

A typical time for cure of curable compositions as described in the present text used for dental applications is within 20 min, or preferably within 10 min, after mixing the components of the composition.

The material is generally regarded as cured, if the cured material fulfils the requirements for its use. For example, a dental precision impression material typically fulfils the requirements for its use when it fulfils the requirements of ISO 4823:2000 (such as compatibility with gypsum, strain in compression, recovery from deformation, detail reproduction, linear dimensional change).

According to a preferred embodiment, the invention is directed to a kit of parts for conducting a dental retraction process, the kit of parts comprising a Base Paste (B) and a Catalyst Paste (C), Base Paste (B) comprising a cationically hardenable component comprising a backbone with polyether moieties and two cationically curable aziridino side groups connected to the backbone, and a porous water-adsorbing component being selected from molecular sieves, zeolites, silica gel and mixtures thereof, Catalyst Paste (C) comprising a starter component being selected from Lewis acids, Broensted acids, precursors of Lewis acids, and components which can be activated by radiation to produce a Lewis acid, salts and mixtures thereof, and water, wherein the Base Paste (B), the Catalyst Paste (C), the cationically hardenable components, the starter component and the water-absorbing component being as described in the present text.

The invention is also directed to a process for taking a dental impression including sub-gingival parts and/or conducting a dental retraction.

Such a process typically comprises the steps of:
  providing a kit of parts comprising the Base Paste (B) and Catalyst Paste (C) as described in the present text,
  combining the Base Paste (B) and Catalyst Paste (C) to obtain dental composition (I),
  applying dental composition (I) to dental tissue (e.g. on the surface of a prepared dental situation in the mouth of a patient and/or in the sulcus of a prepared dental situation in the mouth of a patient),
  letting dental composition (I) harden,
  optionally applying another dental composition (II) being different from dental composition (I) obtained by combining the Base Paste (B) and Catalyst Paste (C),
  removing the hardened dental composition (I) obtained by combining the Base Paste (B) and Catalyst Paste (C) from the dental surface, optionally together with dental composition (II).

The other dental composition (II) is typically also a composition being obtainable from combining a base paste and a catalyst paste, wherein the components of the base and catalyst paste are the same as described above for Base Paste (B) and Catalyst Paste (C).

Dental composition (II) does not contain a water-adsorbing component being present in dental composition (I) and is typically also free of added water.

Dental composition (II) typically differs from dental composition (I) with respect to at least one or more or all of the following features:
  consistency according to ISO 4823;
  starter component;
  filler content.

The consistency according to ISO 4823 of dental composition (II) is typically higher in mm (meaning lower viscosity), e.g. by at least 2 mm compared to the consistency according to ISO 4823 of dental composition (I).

The starter component contained in dental composition (II) is typically a Lewis acid, with a lower water-solubility compared to the starter component contained in dental composition (I).

Conducting the above described process can help reducing and thus simplifying the steps to be conducted by the practitioner during a dental impression procedure where the recording of the surface of the dental tissue beyond the gumline is desired and/or needed.

Dental composition (I) is applied into the sulcus of a prepared dental situation and exerts pressure on the surrounding tissue. After hardening of dental composition (I), a dental composition (II) is applied on top of the visible surface of dental composition (II). Dental composition (II) is not only used for recording the surface of the prepared dental preparation above the gumline but also for removing dental composition (II) from the sulcus of the preparation.

All components used in the dental composition of the invention should be sufficiently biocompatible, that is, the composition should not produce a toxic, injurious, or immunological response in living tissue.

According to one embodiment, the composition described in the present text is characterized by either one or more or all of the following features:
the Base Paste not containing added water;
the Base Paste not containing added acidic compounds;
the Catalyst Paste not containing components being able to chemically react with the water being present in the Catalyst Paste.

The complete disclosures of the patents, patent documents, and publications cited herein are incorporated by reference in their entirety as if each were individually incorporated.

Features and advantages of this invention are further illustrated by the following examples.

The Examples are in no way intended to be limiting thereof. The particular materials and amounts thereof recited in these examples, as well as other conditions and details, should not be construed to unduly limit this invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Method for Determining Total Pore Volume, Average Pore Diameter and BET Surface Area If desired, the total pore volume and average pore diameter can be analyzed with the use of $N_2$ sorption Isotherms and BET surface area analysis. Samples of around 0.3-0.5 grams are cut if necessary from larger samples in order to be inserted in to the straight tubes. All samples are degassed for more than 1 day at 100° C. before analysis. The samples are then analyzed by adsorption and desorption of $N_2$ gas with a Quantachrome Autosorb IQ (Quantachrome Instruments, Florida, USA) in a 12 mm cell with no bulb and without a rod. Absorption data points are collected from 0.0003 to 0.995 P/P0 and desorption points collected from 0.995 to 0.05 P/P0. The analysis is duplicated (or triplicated if repeatability was not ideal), and the averaged results reported. The specific surface area S is calculated by the BET method (Details 10 regarding calculation see Autosorb-1 Operating Manual Ver. 1.51 IV. Theory and Discussion; Quantachrome Instruments, Inc.). The total pore volume $V_{liq}$ is derived from the amount of vapor adsorbed at a relative pressure close to unity (p/p0 closest to 1), by assuming that the pores are then filled with liquid adsorbate (Details regarding calculation see Autosorb-1 Operating Manual Ver. 1.51 IV. Theory and Discussion; Quantachrome Instruments, Inc.). The average pore diameter (d) is calculated from the surface area (S) and the total pore volume $V_{liq}$:

$$d = \frac{4V_{liq}}{S}.$$

Total pore volume and average pore diameter are reported as determined by Nonlocal Density Functional Theory method.

The pore size and BET values mentioned in the Tables below for the various porous components have been taken from the respective description provided by the supplier.

Particle Size

If desired, the particle size can be determined by laser diffraction using a Cilas 1064 Granulometer in "Dry Mode". Results are calculated using the Fraunhofer approximation without Mie correction.

pH value

If desired, the pH value of the filler components can be determined as follows: 5.0 g filler is dispersed in 60 ml methanol. 50 ml distilled water is added. A calibrated pH electrode is dipped into the suspension and the suspension is stirred for 5 min. The pH value is determined 1 min after stirring has been stopped.

Ease of Mixing

The ease of mixing was determined as followed: Pastes B and C are placed on a mixing block in a weight to weight ratio of B:C=3:1. The pastes are mixed/kneaded by hand wearing gloves. After 30 sec the mixed paste should be homogenous and having a mouldable and smooth consistency. Ratings: homogenous, mouldable and smooth consistency: "+++", "++"; Crumble, not mouldable consistency: "---"; "--".

Viscosity

If desired, the viscosity can be measured at 23° C. using a Haake Rotovisco™ 1 device with a plate/plate system (diameter 20 mm) and a slit of 0.2 mm. The viscosity values (Pas) and share stress values (Pa) can be recorded for each share rate (starting from 10 l/s to 110 l/s in 10 l/s steps. For each share rate, a delay of 5 s was used before collecting data. The above mentioned method of measurement corresponds essentially to DIN 53018-2.

Consistency

Consistency of the composition was determined according to ISO 4823:2007-10. If the consistency is to be determined for a single paste, the same procedure is applied, however, leaving out the steps of mixing the pastes and waiting at least 15 min for the material to fully cure before measuring the diameter of the composition under a predefined load.

Setting Time

The setting time of the compositions was determined by measuring the tan δ (delta) value of the mixed base and catalyst paste in dependence on the time at 23° C. and 50% humidity by using a MCR 300 rheometer (plate/plate measurement system) from Anton Paar company. The setting time "tE" and the working time "tA" were determined with the software supplied with the instrument using a curve analysis via tangent method. As known to the skilled person in the art, the tan δ value is the quotient of the plastic and elastomeric portion of the composition.

Shore Hardness

The Shore hardness A was determined according to DIN 53505:2000-8 using a "Härteprüfgerät Zwick 3100/Prüfeinfichtung 7206" (Zwick GmbH & Co. Ulm) as the measuring device.

Residual Gap Measurement

The capability of a curable paste to open a sulcus and to keep a sulcus open during setting time of the paste can be determined by a device using a stamp which creates pressure created by a spring onto the curable paste in a small slit (residual gap device).

More precisely, the method can be described as follows:

A mold having a rectangular shape with the dimensions: x (depth)=7.5 mm, y (width)=18.0 mm and z (height)=12.0 mm is provided.

The mold (1) is formed by three immovable sidewalls (1*a*), (1*b*), (1*c*) and one movable sidewall (1*d*), all located on a plane surface (2). The movable sidewall (1*d*) is equipped with a spring (3) having a defined spring pressure of 20N. The spring is compressed and fixed by a removable fixation means (4). The moveable sidewall (1*d*) is adjusted to a pre-defined depth of 7.5 mm (x-direction). A device for determining the consistency is shown in FIG. 1.

The mold is filled with the curable composition.

After a pre-defined time T1, the fixation means (4) of the spring (3) is removed having the result that the spring (3) exerts a predefined pressure on the curable composition through the movable sidewall (1*d*). A portion of the curable composition is pressed out of the mold (1). The depth of the mold is decreasing which can be determined by measuring the distance for x (mm) using e.g. a length gauge (5).

After a pre-defined time T2, the value for x (mm) is determined.

The higher the value x at time T2 is, the higher the consistency/residual gap behavior of the composition is.

For all results reported below, T1=60 s from start of mixing; T2=70 s from start of mixing.

Figure 2:
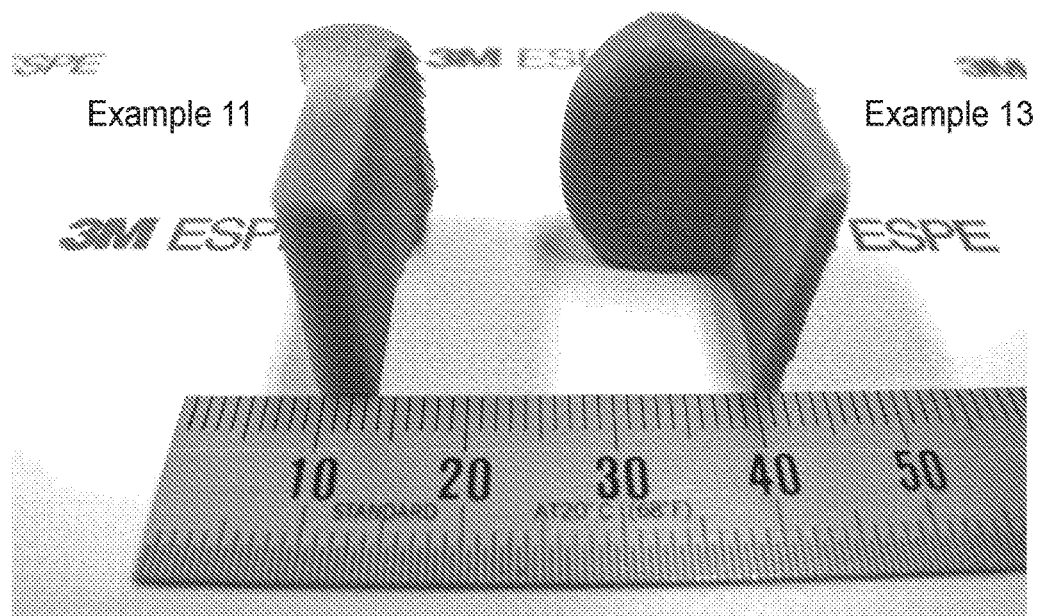
FIG. 2 shows two samples of hardenable compositions which have been analysed with respect to the residual gap behaviour by using the device shown in FIG. 1.

Results and samples obtained by this method are shown in FIG. 2 for the compositions according to Examples 11 and Comparative Example 13.

Materials Used

The following materials were used:

TABLE 1

| Name | Description | Availability |
| --- | --- | --- |
| Aziridino polyether (APE) | Mn: about 6,000 (from EO (ethylene oxide) I THF (tetrahydro furane); obtainable as described in DE 1 745 810 A1 (corresponding to U.S. Pat. No. 3,453,242), Example 20 | |
| EO/PO block copolymer (CAS No. 9003-11-6) | Blockcopolymer (dyn. viscosity at 25° C. = 1,600 mPa * s) | Sigma Aldrich |
| Diatomaceous earth (DE) | Filler | |
| Lauryl imidazole | Retarder | |
| p-toluene sulfonic acid | Starter component | Sigma Aldrich |
| Mineral Oil | Softener (dyn. viscosity at 20° C. = 170 to 230 mPa * s) | |
| Purmol ™ X-Mol | Zeolite; BET surface: >300 $m^2/g$ | Zeochem |
| Purmol ™ 4ST | Zeolite; BET surface: >300 $m^2/g$ | Zeochem |
| Purmol ™ 13X | Zeolite; BET surface: >300 $m^2/g$ | Zeochem |
| Silicagel ™ 60 | Silicagel; BET surface: about 500 $m^2/g$ | Merck |
| Sipernat ™ 50 | Precipitated silica; BET surface: about 500 $m^2/g$ | Evonik |
| AeroSil ™ OX 50 | Pyrogenic silica; BET surface: about 50 $m^2/g$; no pores | Evonik |
| CaO | BET surface: <10 $m^2/g$ | Sigma Aldrich |
| ZnO | Antacid component; BET surface: <10 $m^2/g$ | |
| Impregum ™ Soft Catalyst Paste | Aziridino-Polyether (lot#510417) | 3M ESPE |

Preparation of Base Pastes

Base Pastes B1-B9 were prepared by mixing the following components in a dissolver under thermoregulation:

TABLE 2

| B1 (C.E.) | B2 | B3 | B4 |
| --- | --- | --- | --- |
| 50.7 g APE | 50.7 g APE | 50.7 g APE | 50.7 g APE |
| 34.0 g DE | 34.0 g DE | 34.0 g DE | 34.0 g DE |
| 0.1 g Retarder | 0.1 g Retarder | 0.1 g Retarder | 0.1 g Retarder |
| 0.8 g Pigment | 0.8 g Pigment | 0.8 g Pigment | 0.8 g Pigment |
| 8.3 g Mineral Oil | 8.3 g Mineral Oil | 8.3 g Mineral Oil | 8.3 g Mineral Oil |
| | 10.0 g Zeolite X-mol, pore size 0.3 nm (=3 Ångström); BET: >300 $m^2/g$ | 10.0 g Zeolite 4ST, pore size 0.4 nm (=4 Ångström) BET: >300 $m^2/g$ | 10.0 g Zeolite 13X, pore size 1 nm (=10 Ångström) BET: >300 $m^2/g$ |

TABLE 3

| B5 | B6 | B7 (C.E.) |
| --- | --- | --- |
| 50.7 g APE | 50.7 g APE | 50.7 g APE |
| 34.0 g DE | 34.0 g DE | 34.0 g DE |

TABLE 3-continued

| B5 | B6 | B7 (C.E.) |
|---|---|---|
| 0.1 g Retarder | 0.1 g Retarder | 0.1 g Retarder |
| 0.8 g Pigment | 0.8 g Pigment | 0.8 g Pigment |
| 8.3 g Mineral Oil | 8.3 g Mineral Oil | 8.3 g Mineral Oil |
| 10.0 g Silicagel ™ 60, pore size about 6 nm | 3.0 g Sipernat ™ 50, pore size 3-100 nm | 10.0 g Aerosil ™ OX 50, no pores |
| BET: about 500 m²/g | BET: about 500 m²/g | BET: about 50 m²/g |

TABLE 4

| B8 (C.E.) | B9 (C.E.) |
|---|---|
| 50.7 g APE | 50.7 g APE |
| 34.0 g DE | 34.0 g DE |
| 0.1 g Retarder | 0.1 g Retarder |
| 0.8 g Pigment | 0.8 g Pigment |
| 8.3 g Mineral Oil | 8.3 g Mineral Oil |
| 10.0 g CaO | 6.0 g Diatomaceous earth, pore |
| BET: <10 m²/g | size 500-2200 nm (5000-22000 Ångström); BET: <10 m²/g |

Preparation of Catalyst Paste C1

The following components were mixed: 18.0 g p-Toluenesulfonic acid; 5.0 g water; 41.9 g EO/PO block copolymer; 5.0 g Mineral Oil; 4.5 g ZnO; 30.5 g Diatomaceous earth; 0.1 g Pigment Examples 1-4

3 g Base Paste was mixed by hand kneading using gloves with 1 g Catalyst Paste (C) for 30 sec.

The composition(s) were analyzed with respect to consistency, ease of mixing, setting time, Shore hardness and residual gap performance.

TABLE 5

| | Example | | | |
|---|---|---|---|---|
| | 1 | 2 | 3 | 4 |
| Catalyste paste | C1 | C1 | C1 | C1 |
| Base paste | B1 (C.E.) | B2 | B8 (C.E.) | B9 (C.E.) |
| Consistency B [mm] | 25.0 | 24.0 | 23.0 | 22.5 |
| Consistency C [mm] | 26.0 | 22.5 | 24.0 | 26.0 |
| Consistency B + C [mm] | 23.0 | 18.0 | — | 20.0 |
| Beginning/End of setting [min] | 1.3/2.7 | 1.5/5.9 | 1.9/4.8 | 1.4/3.1 |
| Shore A after 10 min/24 h | 81/84 | 47/81 | 64/79 | 84/86 |
| Ease of mixing | +++ | +++ | +++ | -- (very firm base paste; difficult to mix) |
| Residual gap [mm] | 1.6 | 3.9 | 1.6 | 2.6 |

Findings:

Example 1

The composition contains water, but no water-adsorbing component. The residual gap behavior is not sufficient.

Example 2

The composition contains water, and a water-adsorbing component. The residual gap behavior is sufficient.

Example 3

The composition contains water, and a CaO as filler. The consistencies of the single pastes (base and catalyst) are similar to the consistencies of the single pastes used in Example 2. The residual gap behavior is not sufficient.

Example 4

The composition contains water, and a diatomaceous earth as filler. The consistency of the base paste was very high. Nevertheless, the residual gap behavior found was not as good as for Example 2.

Examples 5-14

Two Catalyst Pastes C1 and C2 were prepared by modifications of the commercially available catalyst paste of the product Impregum™ Soft Tray (3M ESPE) in the following manner:

| C2 (C.E.) | C3 (inventive) |
|---|---|
| 100 g Impregum ™ Soft catalyst paste | 100 g Impregum ™ Soft catalyst paste |
| 24.0 g Diatomaceous earth | 28.0 g Diatomaceous earth |
| | 5.0 g H₂O |

The Catalyst Pastes were mixed with Base Pastes B1-B7 by hand mixing in the ratio of 3 g Base Paste to 1 g of Catalyst Paste C1/C2.

The composition(s) were analyzed with respect to consistency, setting time, hardness and residual gap performance.

TABLE 6

| | Example | | | |
|---|---|---|---|---|
| | 5 | 6 | 7 | 8 |
| Base paste | B1 (C.E.) | B2 | B1 (C.E.) | B2 |
| Catalyst paste | C2 (C.E.) | C2 (C.E.) | C3 | C3 |
| Consistency B [mm] | 25.0 | 24.0 | 25.0 | 24.0 |
| Consistency C [mm] | 23.0 | 23.0 | 16.0 | 16.0 |
| Consistency B + C [mm] | 23.0 | 23.0 | 24.0 | 23.0 |
| Beginning/End of setting [min] | 1.5/3.0 | 1.6/3.4 | 1.2/2.2 | 1.3/2.7 |
| Shore A after 10 min/24 h | 83/86 | 85/89 | 82/85 | 82/89 |
| Residual gap [mm] | 1.1 | 1.5 | 1.6 | 3.4 |

TABLE 7

| | Example | | |
|---|---|---|---|
| | 9 | 10 | 11 |
| Base paste | B3 | B4 | B5 |
| Catalyst paste | C3 | C3 | C3 |
| Consistency B [mm] | 24.0 | 25.0 | 22.0 |
| Consistency C [mm] | 16.0 | 16.0 | 16.0 |
| Consistency B + C [mm] | 23.5 | 24.5 | 23.0 |
| Beginning/End of setting [min] | 1.2/2.3 | 1.5/3.4 | 1.6/3.0 |

TABLE 7-continued

| | Example | | |
|---|---|---|---|
| | 9 | 10 | 11 |
| Shore A after 10 min/24 h | 84/86 | 83/89 | 81/84 |
| Ease of Mixing | +++ | +++ | +++ |
| Residual gap [mm] | 3.2 | 2.7 | 3.9 |

TABLE 8

| | Example | |
|---|---|---|
| | 12 | 13 |
| Base paste | B6 | B7 (C.E) |
| Catalyst paste | C3 | C3 |
| Consistency B [mm] | 22.0 | 24.5 |
| Consistency C [mm] | 16.0 | 16.0 |
| Consistency B + C [mm] | 22.5 | 20.0 |
| Beginning/End of setting [min] | 1.3/2.6 | 1.3/2.3 |
| Shore A after 10 min/24 h | 84/88 | 87/89 |
| Ease of Mixing | +++ | +++ |
| Residual gap [mm] | 3.6 | 1.6 |

Findings:

Compositions containing porous adsorbing component(s) according to the invention and water separated from each other before use are easy to mix and show an improved residual gap behavior.

The invention claimed is:

1. A kit of parts for preparing a dental retraction composition, the kit of parts comprising:
a Base Paste (B) comprising a cationically hardenable component, the cationically hardenable component comprising a polyether polymer comprising cationically curable side groups,
a Catalyst Paste (C) comprising a starter component selected from Lewis acids, Brønsted acids, precursors of Lewis acids, and components which can be activated by radiation to produce a Lewis acid, salts and mixtures thereof,
a porous water-adsorbing component selected from molecular sieves, zeolites, silica gel, and mixtures thereof, and
water;
wherein:
the porous water-adsorbing component is present in Base Paste (B) and the water is present in Catalyst Paste (C), or
the porous water-adsorbing component is present in Catalyst Paste (C) and the water is present in Base Paste (B).

2. The kit of parts of claim 1, the ratio of porous water-adsorbing component to water being from 1.00:0.50 to 1.00:0.05 with respect to weight.

3. The kit of parts of claim 1, the porous water-adsorbing component being characterized by one or more of the following features:
having a BET surface area of at least 200 m²/g;
average pore diameter: below 100 nm;
average particle size: from 1 to 50 μm; and
pH value: above 7.

4. The kit of parts of claim 1, the cationically hardenable component being characterized by at least of the following features:
the cationically curable side groups being aziridino groups;
being present in an amount from 5 to 90 wt.-% with respect to the weight of a composition obtained by combining Base Paste (B) and Catalyst Paste (C).

5. The kit of parts of claim 1, the starter component being characterized by at least of the following features:
being water-soluble;
being present in an amount from 1 to 30 wt.-% with respect to the weight of a composition obtained by combining Base Paste (B) and Catalyst Paste (C).

6. The kit of parts of claim 1, at least one of Base Paste (B) and Catalyst Paste (C) having a consistency of less than 28 mm determined according to ISO 4823.

7. The kit of parts of claim 1, Catalyst Paste (C) further comprising an antacid compound.

8. A composition obtained by mixing Base Paste (B), and Catalyst Paste (C) of claim 1, the composition being characterized by one or more of the following features:
consistency: less than 26 mm determined according to ISO 4823;
Shore hardness A: from 40 to 90 determined according to DIN 53505 24h after mixing; and
hardening within 15 min within a temperature range from 20 to 40° C. to a rubber elastic mass.

9. The composition of claim 8, comprising the components in the following amounts:
cationically hardenable component: 5 to 90 wt.-%,
starter component: 1 to 30 wt.-%,
porous water-adsorbing component: 1 to 60 wt.-%, and
water: 0.01 to 10 wt.-%,
wt.-% with respect to the weight of the composition.

10. The composition of claim 8, being characterized by one or more as follows:
the cationically hardenable component comprising an aziridino moiety and being present in an amount from 15 to 80 wt.-%,
the starter component selected from Brønsted acids or Lewis acids and being present in an amount from 2 to 20 wt.-%,
the water-adsorbing component being present in an amount from 2 to 20 wt.-%, and
water being present in an amount from 0.1 to 5 wt.-%,
wt.-% with respect to the weight of the composition.

11. A method for preparing a dental retraction material, the method comprising:
contacting the Base Paste (B) and the Catalyst Paste (C) of claim 1.

12. A process for taking a dental impression including sub-gingival parts, the process comprising:
combining the Base Paste (B) and Catalyst Paste (C) of claim 1 to form a dental composition (I),
applying the dental composition (I) to a dental tissue,
allowing the dental composition (I) to harden,
applying a dental composition (II) in contact with dental composition (I), and
removing together the dental composition (II) and the dental composition (I) from the dental tissue,
wherein the dental composition (I) and dental composition (II) are comprised of different materials.

13. The kit of parts of claim 1, wherein the combination of the water-adsorbing component and water is effective to increase the consistency, according to ISO 4823, of the hardenable composition.

14. A composition for dental retraction obtained by mixing the Base Paste (B) and the Catalyst Paste (C) of claim 1.

15. A kit of parts for conducting a dental retraction, the kit of parts comprising the Base Paste (B) and the Catalyst Paste (C) of claim 1, wherein:
the Base Paste (B) comprises the porous water-adsorbing component, and
the Catalyst Paste (C) comprises water.

16. The kit of parts of claim 7, wherein the antacid is selected from oxides, hydroxides, carbonates, or carboxylates of Zn or Al, or a combination thereof.

17. The kit of parts of claim 1, the polyether polymer being a copolymer of ethylene oxide and tetrahydrofuran.

18. The kit of parts of claim 17, the cationically curable side groups being aziridine groups.

19. The kit of parts of claim 1, further comprising a non-ionic surfactant.

20. The kit of parts of claim 1, further comprising one or more of a retarder, a pigment, and a filler.

* * * * *